United States Patent [19]

Down

[11] Patent Number: 5,417,647
[45] Date of Patent: May 23, 1995

[54] SUPPORT FOR BEHIND THE KNEE JOINT

[76] Inventor: James W. Down, 1605 Keokee St., Adelph, Md. 20783

[21] Appl. No.: 233,242

[22] Filed: Apr. 26, 1994

[51] Int. Cl.⁶ .................................................. A61F 5/00
[52] U.S. Cl. ........................................ 602/26; 602/62; 2/16; 2/24; 2/62
[58] Field of Search .............. 602/26, 5, 20, 23, 61, 602/62, 63; 606/201, 203, 204; 2/16, 24, 59, 62; 482/105; 128/869, 876, 878, 881, 882

[56] References Cited

U.S. PATENT DOCUMENTS

| | | | |
|---|---|---|---|
| 2,179,903 | 11/1939 | Spears | 602/26 |
| 2,607,920 | 8/1952 | Lawrence | 2/62 |
| 3,712,299 | 1/1973 | Voehl | 2/24 X |
| 3,888,244 | 6/1975 | Lebold | 602/62 X |
| 4,240,414 | 12/1980 | Theisler | 602/26 |
| 4,243,028 | 1/1981 | Puyana | 602/62 |
| 4,247,101 | 1/1981 | Gallmeyer | 482/105 X |
| 4,333,181 | 6/1982 | Corriero | 602/26 X |
| 4,334,528 | 6/1982 | Gauvry | 602/26 |
| 4,532,921 | 8/1985 | von Turklus et al. | 602/26 |

*Primary Examiner*—Linda C. M. Dvorak
*Attorney, Agent, or Firm*—Robert Halper

[57] ABSTRACT

A mechanical device for alleviating pain from swelling caused by Baker's cysts and the like comprising a rigid arcuate tubular element placed in the cavity behind the knee joint and fastened by straps placed over the knee at the femur and the tibia.

5 Claims, 1 Drawing Sheet

U.S. Patent     May 23, 1995     5,417,647
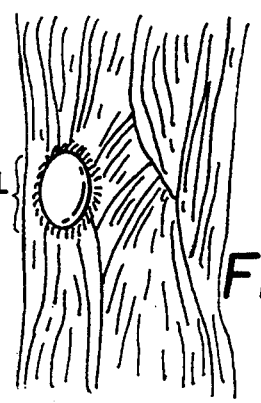
FIG. 2
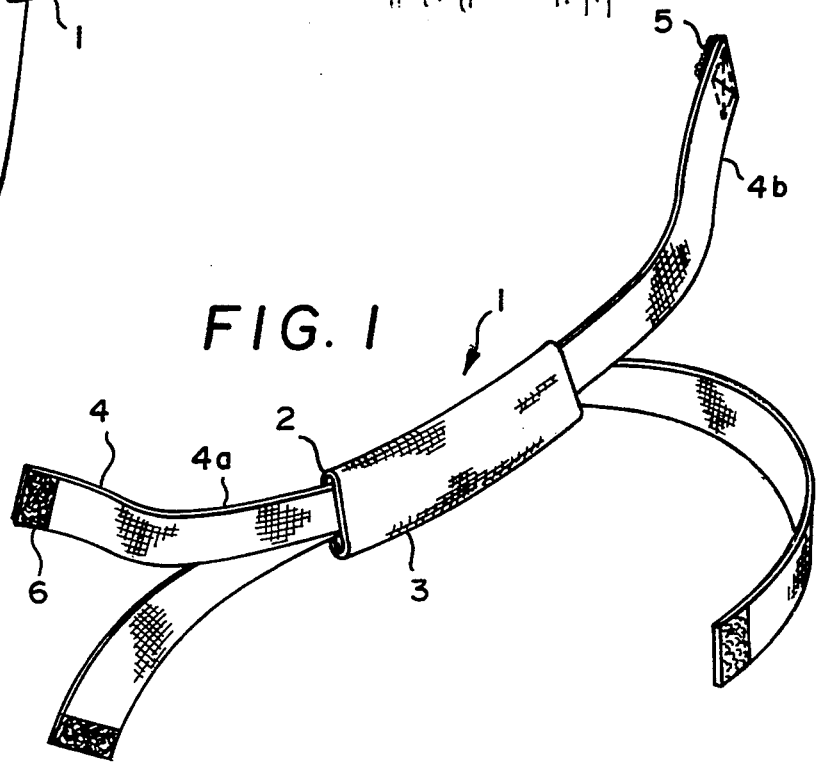
FIG. 5
FIG. 1
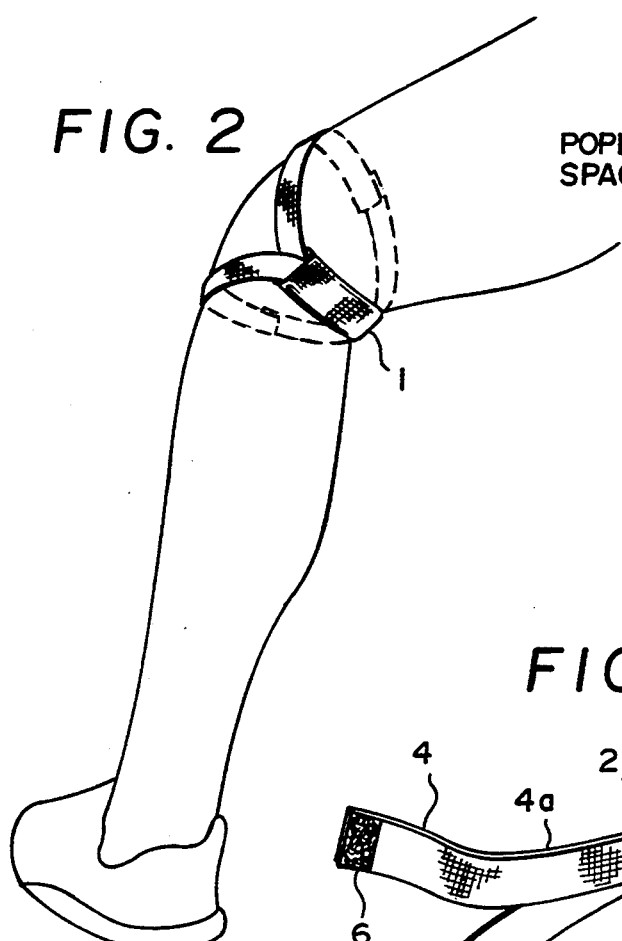
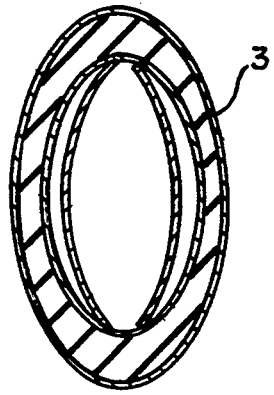
FIG. 4
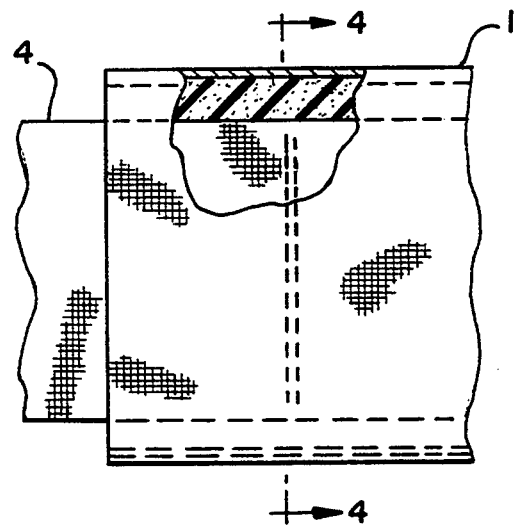
FIG. 3

SUPPORT FOR BEHIND THE KNEE JOINT

FIELD OF INVENTION

This invention has to do with a support behind a knee joint, one which has been found particularly helpful for people who suffer from Baker's cysts or other painful inflammations.

BACKGROUND OF THE INVENTION

While there are a number of supports or bandages for assisting people with knee ailments, generally these supports are designed to treat areas around the patella or kneecap. On the other hand, there are patents that do control swelling such as caused by a hernia or in a wrist, ankle or similar joint, but these are structurally different from the device of the instant invention.

U.S. Pat. No. 4,334,528 is exemplary of a knee strap for treating chondromalacia patella. Strip 12 includes a pair of end portions 14 and 16 about two inches in height and about a quarter inch thick. End portion 14 has a velcro pad sewn therein and 16 has a cloth material made of tricot which cooperates with the VEL-CRO® to fasten the ends together at the posterior region of the knee joint. Between ends 14 and 16 is located a rounded center portion 20 that incorporates a latex tube which while more rigid than the ends is still somewhat flexible. The rubber tube is enclosed in a cloth tube sewn together by stitching. This tube is placed just below the kneecap. When the strap is in place the tube controls the patella tendon.

U.S. Pat. No. 4,532,921 is a knee joint bandage that comprises a knee hose 1 made of elastic fabric and having a conical, shape to take into consideration that the upper leg has a greater diameter than the lower leg. A tubular holder 2 that acts as a guide is sewn into the hose 1. It may be made of the same material as the hose or it could be made of leather. A support strap 3 extends through the holder. The middle portion of the strap may be a leather jacket or also made of elastic material. The jacket has a filling of felt. The middle of the jacket curves downwardly like the tubular holder 2 to provide the maximum possible wide support. In use the hose is pulled through the foot and lower leg upwardly so that the support strap 3 lies in a groove shaped cavity below the knee disk 10. The purpose of the bandage is to provide a knee joint bandage with which the knee joint is unloaded during working and movement of the knee. The bandage then compensates for the lack of a smooth gliding face of the knee disk because of general deterioration or gristle loosening.

U.S. Pat. 2,559,514 while not directed to alleviating knee pain is cited for the showing of using two strips 7 and 8 to fasten an arm shackle placed around the arm elbow, one strip being placed around the arm above the shackle and one strip being placed around the arm below the shackle.

U.S. Pat. 1,925,615 shows a hernia pad 10 and a mounting base 11 to which is attached a truss 12 in the form of a resilient wire bent halfway around the body in such a way that the pad may oscillate to produce a massage-like movement. The wire ends in a small cushion or pad 13 that engages the body rearwardly of the hip so as to exert pressure under strain of the member 12 to draw the pad against the hernia. The pad 10 is cemented to the base. The pad may be of hard rubber while the base is formed hard wood. The base and the pad 10 are oval in shape and the pad is hollow, but has an aperture for discharging emollient contained in the pad. The pad is received by an annulus 15 that has an aperture 16 through which the pad is inserted. The annulus has extensions 17, 18 and 19 which are coated with adhesive for holding the pad in place.

U.S. Pat. 2,445,173 is a joint brace for reducing swellings in the finger, wrist, ankle or similar joint. It comprises a flexible band 10 constructed of layers of cloth or other similar material. The edge portions of the layers are stitched together with stitching 11 and the band is adapted to be engaged over one's joint or limb. There is a tab 12 for gripping the band to assist in its positioning about the finger or limb. A support strip 13 of flexible metal is adjustably mounted between the layers 10 and has its ends 14 rolled and extended through a slot in the outermost layer of 10.

U.S. Pat. 4,243,028 is a therapeutic pressure strap for treating tennis elbow. It consists of a flexible inelastic band having fastening means at both ends for securing around the extremities of a person. On the inside of the strap is a pocket 26 in the form of a semi-cylinder. Within the pocket are a pair of resilient cylinders for applying pressure. They can be either solid or hollow depending on the amount of applied pressure.

SUMMARY OF THE INVENTION

The invention concerns a support placed in the popliteal space behind the knee joint and is designed to alleviate pain because of pressure or muscle spasms or swelling behind the knee. Essentially the device is a rigid tubular member that fits into the cavity behind the knee joint and is fastened by two straps that pass through the tube and are fastened both above and below the knee.

Swelling behind the knee is caused quite often by what is known as Baker's cysts. Baker's cysts occur when there are tumors in the popliteal space. The cause of these cysts is probably that of normal anatomic connection aggravated by chronic effusion of the intra-articular joint cavity. Chronic effusion may be caused by rheumatoid arthritis, meniscus tearing, cruciate ligamentous tears.

To date the standard remedy for such swelling behind the knee has been pain relievers supplemented by antibiotics to fight infection or surgical removal of the cysts. This invention offers a simple mechanical device as an alternative to the presently known methods of treatment. It has been found that in a number of days within application of this device the pain has subsided and the swelling is appreciably diminished.

BRIEF DESCRIPTION OF THE DRAWINGS

FIG. 1 is a front elevation view of the apparatus.
FIG. 2 is an assembly showing the support fastened behind the knee joint.
FIG. 3 is an end view of the apparatus.
FIG. 4 is a side view of the apparatus.
FIG. 5 is a view showing the cyst located behind the knee joint.

DETAILED DESCRIPTION OF THE PREFERRED EMBODIMENT

FIG. 1 shows a support 1 that comprises a tubular member 2 dimensioned so as to the length of the circumference of the cavity behind the knee joint. The tubular member is made of a hard, rigid material which may be a rubber or plastic such as used in pressurized connections. It is covered completely with a soft textile 3 such as cotton or a synthetic, which is bonded to the tube. The tubular member has a slight curve with a radius of curvature that approximates the curvature of the cavity behind the knee joint. The outer diameter of the tube is about 1 inch and the inner diameter about ¾ inch. Press fitted through the tube so as to extend equally from each end of the tube are two identical straps 4, each strap being about ⅞ inch wide. The straps may be stitched together in the region that passes through the tube so as to keep them in alignment without one strap extending beyond the other, although in view of their width, there is no need to fasten them to the tube itself. The major portions of the straps 4a, that is the portion that extends continuously to the end portions, are made of elastic material, but the end portions 4b are provided with fasteners. One of the end portions has stitched on its inner face a hook and loop portion 5 known as VEL-CRO®, while the other end portions have stitched on its outer face a fibrous material 6 to which the hook and loop portions adhere. The straps are made long enough to fit around the knees and because of the elastic portions can easily be adjusted to various size knees. In use the tubular support is placed in the cavity behind the knee joint so that its concave portion rests directly therein. The support is then fastened with one strap passing over the leg at the femur and one strap passing over the leg at the tibia. The straps are made tight enough so as to apply moderate pressure in the afflicted area. While the apparatus has been designed for placement behind the knee joint, it could readily be adapted to fit in other cavities that might develop swelling such as behind the finger joint.

While a specific embodiment of the invention has been illustrated, it is to be understood that many changes and modifications can be made without departing from the spirit of the invention as defined in the following claims.

I claim:

1. A knee support for treatment of pain in the popliteal space behind the knee joint comprising a hard, rigid, arcuate tubular element dimensioned to extend across the circumferential behind the knee joint between the femur and the tibia, said tubular element having a pair of fastening straps extending through said tubular element, a major portion each of said straps being made of elastic material said straps having ends that are adapted to pass around the knee, one of said ends of each strap having hook and loop material on its underface for fastening to a cloth material on its upperface on said other of said ends, one of said straps being adapted for fastening above the knee joint and the other of said straps being adapted for fastening below the knee joint, said major portion being a continuous length of elastic material that extends to said ends.

2. A support as in claim 1 wherein said tubular element is made of hard rubber and is completely covered with a layer of soft textile material.

3. A support as in claim 1 wherein the tubular element is made of hard plastic and is completely covered with a layer of soft textile material.

4. A support as in claim 1 wherein the inner diameter of said tubular element is about ¾" and the width of said straps is about ⅞" said straps being stitched together in the section that passes through said tubular element, the straps being secured fast in the tubular element without adhesives by a press fit.

5. A support as in claim 1 wherein the radius of curvature of said tubular element approximates that of the cavity behind the knee joint in which the concave portion of the tubular element is located and the ratio between the length of the tube to its inner diameter is at least 4:1.

* * * * *